(12) United States Patent
Harrah

(10) Patent No.: US 6,360,031 B1
(45) Date of Patent: Mar. 19, 2002

(54) OPTICAL WAVEGUIDE SENSORS

(75) Inventor: Larry A. Harrah, Albuquerque, NM (US)

(73) Assignee: Adherent Technologies, Inc., Albuquerque, NM (US)

( * ) Notice: Subject to any disclaimer, the term of this patent is extended or adjusted under 35 U.S.C. 154(b) by 0 days.

(21) Appl. No.: 09/379,706

(22) Filed: Aug. 24, 1999

(51) Int. Cl.$^7$ .................................................. G02B 6/00
(52) U.S. Cl. .......................... 385/12; 385/127; 385/38
(58) Field of Search ............................ 385/12, 127, 38

(56) References Cited

U.S. PATENT DOCUMENTS

| | | | |
|---|---|---|---|
| 4,846,548 A | * | 7/1989 | Klainer |
| 5,268,972 A | | 12/1993 | Tabacco et al. |
| 5,286,777 A | | 2/1994 | Schoeler et al. |
| 5,307,146 A | | 4/1994 | Porter |
| 5,343,550 A | * | 8/1994 | Egalon et al. |
| 5,446,280 A | | 8/1995 | Wang et al. |
| 5,563,967 A | | 10/1996 | Haake |
| 5,704,890 A | | 1/1998 | Bliss et al. |

OTHER PUBLICATIONS

Guthrie, A.J., et al., "Solid–State Instrumentation for Use with Optical–Fibre Chemical–Sensors," *Talanta*, vol. 35, o. 2, pp 157–159 (1988).

Smardzewski, RR., "Multi–Element Optical Waveguide Sensor: General Concept and Design," *Talanta*, vol. 35, No. 2, pp 95–101 (1988).

* cited by examiner

*Primary Examiner*—Hung N. Ngo
(74) *Attorney, Agent, or Firm*—Jeffrey D. Myers; Rod D. Baker; Brian J. Pangrle

(57) ABSTRACT

An optical waveguide sensor using an intermediate layer between the preformed optical core and the optical cladding material. This intermediate layer comprises a material that is doped with a sensor material to respond to an analyte of interest by luminescing or by developing optical absorption in the transmission region of the core fiber and that has a refractive index greater than the preformed core. Two configurations provide sensors for ionizing radiation capable of measuring the dose rate and the integrated deposited dose.

20 Claims, 3 Drawing Sheets

OPTICAL WAVEGUIDE SENSORS

BACKGROUND OF THE INVENTION

1. Field of the Invention (Technical Field)

The present invention relates to optical sensors.

2. Background Art

Fiber optic sensors have been used for analytical purposes for a number of years. In their usual realizations, they use either the optical and physical properties of the fiber core material or that of the lower index internally reflecting cladding to develop a response. Responses that have been used include: direct optical absorption of transmitted light by the core material; absorption produced in the reflective cladding material that attenuates the transmitted light in the core by reducing interface reflectivity; changes in the refractive indices of the cladding or core leading to changes in light transmission sensed by interferometry; or the development of fluorescence in the core material or some reagent situated at the core terminus.

In some of these realizations, strain induced by sorption of the analyte in either the cladding or the core lead to responses measured interferometrically. Fiber optic strain gauges have been constructed in which the material properties are altered mechanically.

Generally, fiber optic sensors are constructed by altering the optical core, the cladding material, or sometimes even the outer protective layer to give an optically detected response in some defined region of the optical fiber's length. Sensors that result in a modification of the core material's optical properties are the most sensitive, but are also the most difficult to manufacture. Doping the core with a sensing reagent that indicates an environmental change necessitates fabricating the light guide from doped, bulk material and providing a cladding that transmits the analyte of interest. U.S. Pat. No. 5,286,777, to Schoeler et al., entitled "Preparing a dye-containing polymer," discusses a method for producing doped core material for incorporation into a fiber optic sensor element. Changes in the optical properties of the sensing reagent induced by the environmental analyte are then measured as changes in light transmission of the fiber.

As mentioned above, custom fabrication of the fiber optic core can be difficult and consequently drives up sensor costs. Utilizing sensing reagents incorporated in the cladding material is considerably less expensive, and works by altering the optical properties of the fiber by a process called "frustrated" or "attenuated" internal reflection. These sensing layers are directly exposed to the environment and can be applied after fiber manufacture. Smardzewski (Talanta, Vol. 35, No.2, pp. 95–101 (1988)) discusses such a sensor in which the fibers are replaced by optical waveguides externally coated with an analyte sensitive cladding. U.S. Pat. No. 5,268,972, entitled "Aromatic Hydrocarbon Optrodes for Groundwater Monitoring Applications," to Tabacco, et al., issued Dec. 7, 1993, discusses a sensor constructed with porous cladding material whose refractive index is modified by absorption of aromatic hydrocarbons resulting in reduced transmission by attenuation of the sensing light. However, choices of sensing reagent are limited by the rigorous optical requirements for cladding materials. For most organic fibers or fused silica, cladding with either fluorocarbons or silicones is necessary to provide a lower index of refraction. These materials are poor solvents for most complex organic sensing reagents or analytes.

In addition to the aforementioned materials considerations, there are other issues involved in fiber optic sensor production. Often, special fibers (either modified core or modified cladding) must be produced for the active sensor region and then coupled to inactive fiber optic lead(s) following production. The coupling of the sensing segment to the leads often is a limiting factor in sensitivity, reproducibility or device fabrication. Typical of this type of sensor, is the "Real Time Sensor for Therapeutic Radiation Delivery", U.S. Pat. No. 5,704,890, to Bliss, et al., issued Jan. 6, 1998. In this device, the fiber optic leads are coupled to a scintillator (or scintillator segments) and serve to collect and transmit the scintillations to the detector. A limitation of this device is the necessity to carefully adjust the refractive indices of the scintillator material to that of the fiber optic leads to ensure efficient collection of light. Guthrie et al. (Talanta, Vol. 35, No. 2, pp. 157–159 (1988)) also describe an extrinsic sensor where the sensing element is a film sensitive to the pH of the solution in which it is immersed. The fiber optic leads serve to read changes in the color of the pH sensitive film.

Device calibration may also be an issue. U.S. Pat. No. 5,307,146, entitled "Dual-Wavelength Photometer and Fiber Optic Sensor Probe," to Porter, et al., issued Apr. 26, 1994, and U.S. Pat. No. 5,446,280, entitled "Split-Spectrum Self-Referenced Fiber Optic Sensor," to Wang, et al., issued Aug. 29, 1995, teach the necessity to analyze the sensing light at more than a single wavelength in order to achieve long term stability and calibration of the sensor. This places additional requirements on the sensor optical properties if the sensing and reference functions are confined to a single optical waveguide core. U.S. Pat. No. 5,563,967, entitled "Fiber Optic Sensor Having a Multicore Optical Fiber and an Associated Sensing Method," to Haake, issued Oct. 8, 1996, uses two optical waveguides in a single fiber cable to overcome this problem in a device to measure mechanical differences between the sensor and reference elements.

The aforementioned references collectively contain a variety of limitations. Some require complex measurement systems while others require features that limit noninvasiveness. Therefore, a need exists for sensors that are easily instrumented and can operate in a relatively noninvasive manner.

SUMMARY OF THE INVENTION
(DISCLOSURE OF THE INVENTION)

The present invention is of an optical waveguide sensor comprising a waveguide core; a reflective cladding; and at least one intermediate layer positioned between the waveguide core and the reflective cladding comprising a material responsive to at least one environmental stimulus; and wherein refractive indices of the core ($n_1$), the at least one intermediate layer ($n_2$) and the reflective cladding ($n_3$) obey the relationship $n_2 \geq n_1 > n_3$. The at least one intermediate layer comprises a material that produces a response to at least one environmental stimulus that is detectable by electromagnetic absorption and/or electromagnetic transmission. The environmental stimulus is, for example, chemical concentration, ultraviolet radiation and/or ionizing radiation.

The waveguide sensor of the present invention can comprise a segment of a waveguide. In most instances, a waveguide comprises a waveguide core and a reflective cladding; however, any medium in contact with the fiber core that has a refractive index according to $n_3$ of the above-mentioned equation will act, to some degree, as a reflective cladding. For example, when a fiber core is immersed in a medium having a refractive index that is less than that of the fiber core, a wave internal to the fiber core will have a pronounced reflective component. Of course, the present invention is not limited to use of a "fiber" and it is understood that other waveguide geometric configurations are possible, such as, but not limited to, planar waveguides. Furthermore, waveguide sensors of the present invention are useful in a variety of geometric operational configurations, such as, but not limited to, transmission and reflective configurations. In transmission operational configurations, the sensor comprises, for example, at least one segment of a waveguide. In reflective operational configurations, the sensor comprises, for example, a terminal end of a waveguide. In such a configuration, the sensor comprises a reflective cap and at least one intermediate layer positioned between the terminal end of the waveguide core and the reflective cap. As mentioned previously, for operation in a medium having a low refractive index (compared to that of the waveguide core), the need for a reflective cladding is reduced or eliminated. In such instance, a preferred embodiment of the present invention comprises a waveguide core comprising an outer surface and a layer positioned on the outer surface of the waveguide core wherein the layer comprises a material responsive to at least one environmental stimulus. The layer further an outer surface that contacts a medium comprising a refractive index greater than the refractive index of the waveguide core. As for embodiments of the present invention comprising a reflective cladding, the material responsive to at least one environmental stimulus produces a response detectable by, for example, electromagnetic absorption and/or electromagnetic transmission. The material is typically responsive to environmental stimulus such as, but not limited to, chemical concentration, ultraviolet radiation and ionizing radiation. Of course, the sensor may comprise more than one intermediate layer, and such layers may produce responses to the same or different environmental stimuli. Sensors of this particular embodiment are useful in the aforementioned geometric configurations and geometric operational configurations.

Sensors of the present invention may be made according to a method of the present invention for fabrication comprising: providing a waveguide core having an outer surface and affixing an intermediate layer to the outer surface of the waveguide core wherein the intermediate layer comprises a material responsive to at least one environmental stimulus. In certain instances, the method further comprises an additional step of affixing a reflective cladding to the outer surface of the intermediate layer. The method of the present invention is useful for fabricating sensors wherein the material responsive to at least one environmental stimulus produces a response detectable by at least one member selected from the group consisting of electromagnetic absorption and electromagnetic transmission; wherein the material responsive to at least one environmental stimulus produces a response to at least one environmental stimulus selected from the group consisting of chemical concentration, ultraviolet radiation and ionizing radiation; wherein the sensor comprises a segment of a waveguide wherein the waveguide comprises a waveguide core and a reflective cladding; and wherein the sensor comprises a terminal end of a waveguide wherein the waveguide comprises a waveguide core comprising a terminal end and a reflective cladding. For reflective operational configurations, the method comprises steps for affixing a reflective cap such that at least one intermediate layer is positioned between the terminal end of the waveguide core and the reflective cap.

The present invention provides for insertion of at least one cladding layer between a reflective cladding and an optical core material to induce optical absorption directly in the transmitted spectrum. Embodiments comprising an added single cladding are referred to herein as having a dual cladding configuration. Preferred embodiments of the present invention are constructed on a preformed fiber optic light guide without the necessity for connectors to the sensor segment. Optical properties for an intermediate, or "cladding", layer only require a refractive index equal to or greater than that of the original core material. Under this condition, an added intermediate layer becomes part of the optical core, which together form a sensing region. The optical properties of a fiber optic waveguide containing such a sensing region "segment" are described below.

A primary object of this invention is to provide a simple optical waveguide configuration for the construction and manufacture of optical waveguide sensors.

A further object of this invention is to provide a means to render preformed optical waveguides sensitive to environmental components.

Yet another object of this invention is to provide a means for producing optical waveguide sensors without necessity for incorporating connectors between a sensor segment and an optical lead.

An additional object of this invention is to provide sensor configurations sufficiently small to be inserted into a local environment without excessive perturbation of that environment.

The present invention provides several advantages over previously used fiber optical waveguide sensors. Among these are: ease of fabrication on existing, preformed optical fiber; separation of the required physico-chemical properties of the sensor and cladding layers into distinct host polymers; and absence of connectors to attach an active portion of a sensor to at least one optical lead necessary for connection to a remote read-out device. In combination, these advantages reduce production costs of sensors and increase operational flexibility.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

Figure 1:
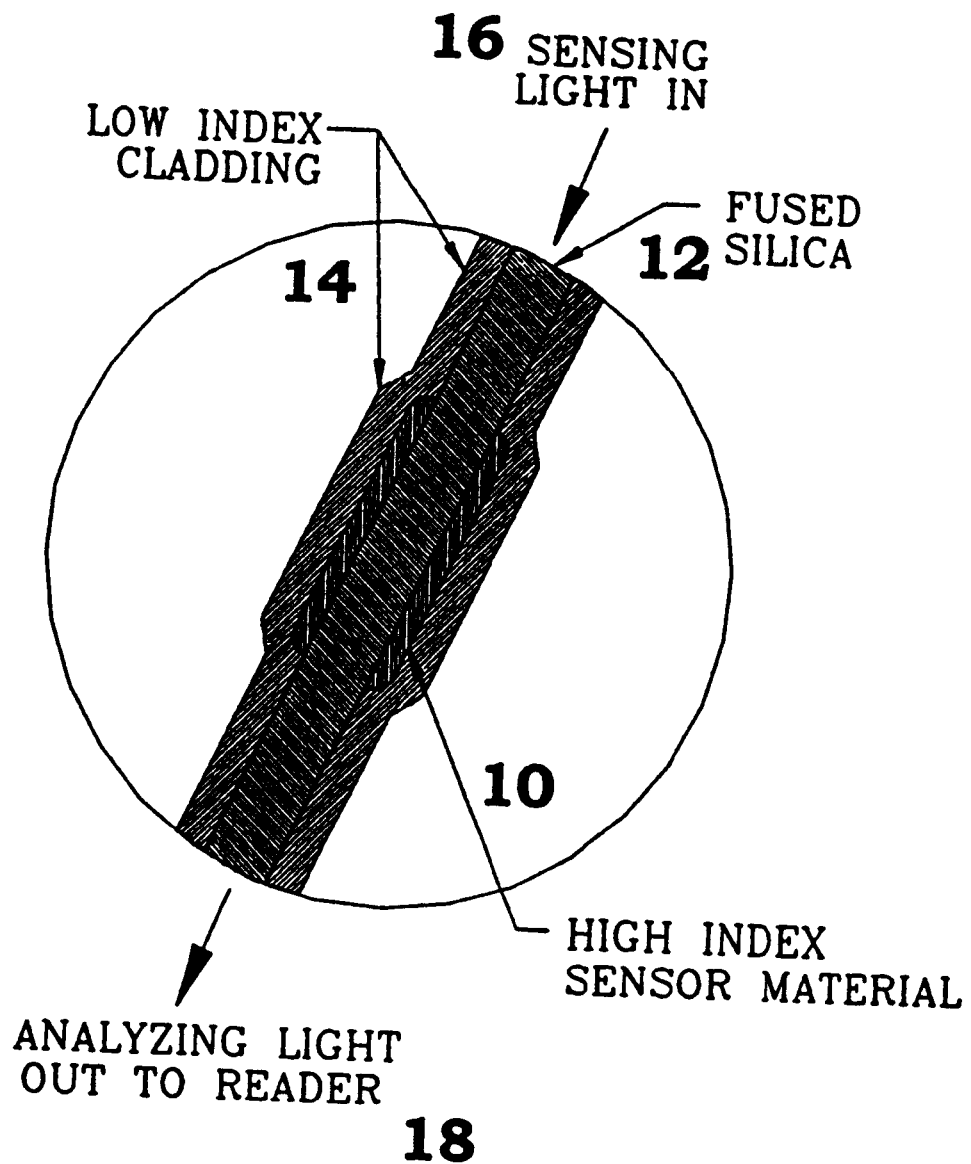
FIG. 1 is an illustration of a preferred embodiment (referred to as a "transmission" configuration) of the present invention. Here a sensor operates in an absorption mode where the sensor layer changes its optical transmission in response to an environmental stimulus of interest.

DESCRIPTION OF THE PREFERRED EMBODIMENTS (BEST MODES FOR CARRYING OUT THE INVENTION)

In the present invention, single optical waveguide configurations are sensitized to environmental variations by removing a region of the reflective cladding and adding a segment of at least one coating, i.e., cladding or intermediate layer, that contains a reagent or activator that responds to at least one desired environmental stimulus, or transformation thereof. This segment is then re-coated with a reflective cladding that allows transmission of at least one desired environmental stimulus. The segment thus produced forms a sensor for at least one environmental stimulus. An environmental stimulus is construed broadly to comprise physical stimuli, chemical stimuli, and stimuli from electromagnetic radiation, including ionizing radiation and heat energy. A reflective cladding comprises material that allows transmission of an environmental stimulus. A reflective cladding can transmit an environmental stimulus in a same chemical and/or physical energy form or it may transmit an environmental stimulus in a different energy form. For example, piezoelectric cladding material can transmit a physical stimulus in the form of an electrical stimulus. Thereafter, the electrical stimulus is transmitted to an intermediate layer, or cladding, that, in turn, responds to the transformed environmental stimulus. When a chemical stimulus is of interest, the reflective cladding comprises, for example, but not limited to, permeability to that chemical and/or an ion-exchange capacity for that chemical. Transport of a chemical environmental stimulus comprises passive transport through a diffusion gradient, facilitated transport, and/or active transport, as those terms are defined in the art.

For some applications, the medium in which the present invention is useful comprises a low refractive index. In such applications, the need for a reflective cladding is eliminated or greatly reduced. Optical sensors for use in such media are within the scope of the present invention. In the descriptions that follow, the low refractive index medium is analogous to material represented by the refractive index $n_3$.

Sensors of the present invention are useful to detect at least one desired environmental stimulus with sensitivity proportional to the length and thickness of the sensor layer and inversely proportional to the thickness of the fiber waveguide core. Preferred embodiments of the present invention comprising this optical waveguide configuration and resulting sensitivity are discussed below.

Applying an intermediate layer with environmental sensitivity in this manner does not interrupt the optical core integrity and does not require connectors between the sensor element and the waveguide leads to the sensor thus simplifying manufacture of the present invention. Application of a layer in this manner allows tailoring of sensitivity of the present invention by altering dimensions of an active layer, changing the mode of core illumination, and/or by changing at least one dimension of the waveguide core. This flexibility provides for a wide range of applications. Furthermore, such an apparatus operates in several modes. The sensor layer may operate in an absorption mode to alter the spectrum or transmission of the sensing light or it may operate by introducing light into the core by luminescence (e.g., fluorescence, phosphorescence, or chemiluminescence of the reagent). In a preferred embodiment, the apparatus is configured as a transmission device wherein sensing light is introduced into one end of the sensing segment and changes in transmission are detected at the opposite end (see FIG. 1).

Figure 2:
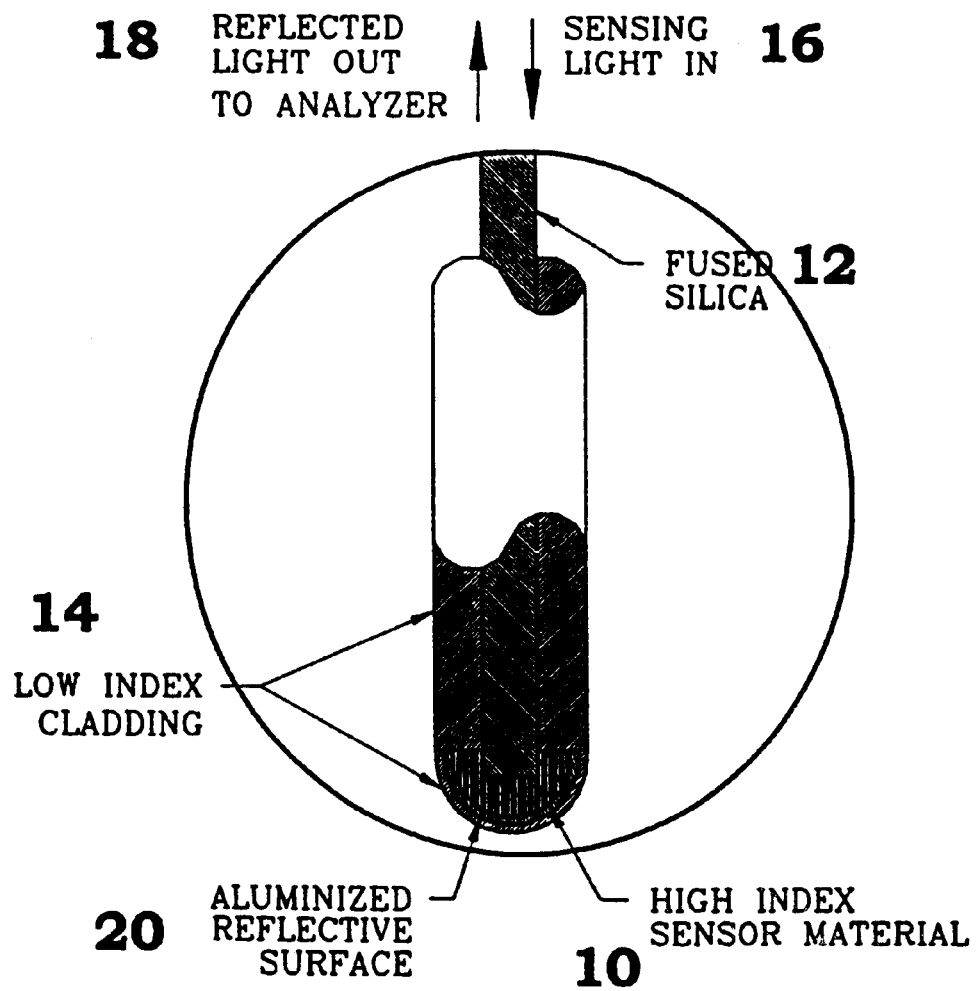
FIG. 2 is an illustration of a preferred embodiment of the present invention operated in a "reflective" configuration. This configuration is useful for absorption and/or luminescence sensing. The small size allows insertion of such a sensor into a local environment without excessive perturbation of that environment. Again, the sensor responds to an environmental stimulus of interest.

In an alternate embodiment, the apparatus is configured in a reflection mode where the sensing and detecting paths originate at the same end of the waveguide (see FIG. 2). This last embodiment requires a directional coupler for the guide to separate the entry and exit paths when used to detect optical absorption. Single ended apparatuses for the detection of introduced luminescence (fluorescence or chemiluminescence) do not require the directional coupler and are most effective when the sensing region is near one end of the waveguide and when the sensor end is coated with a reflective coating.

The dual cladding configuration is effective with many optical core geometries. Planar waveguides, cylindrical waveguides and broadband (multimode) optical fibers may be used with the present invention. The present invention also comprises multiple cladding configurations wherein more than two cladding are used. Such embodiments are useful for simultaneous detection of multiple environmental stimuli and for single desired environmental stimuli wherein application of a single added cladding layer is inefficient or insufficient for detection of a desired environmental stimulus.

Optics of the Dual Clad Segment

Figure 3:
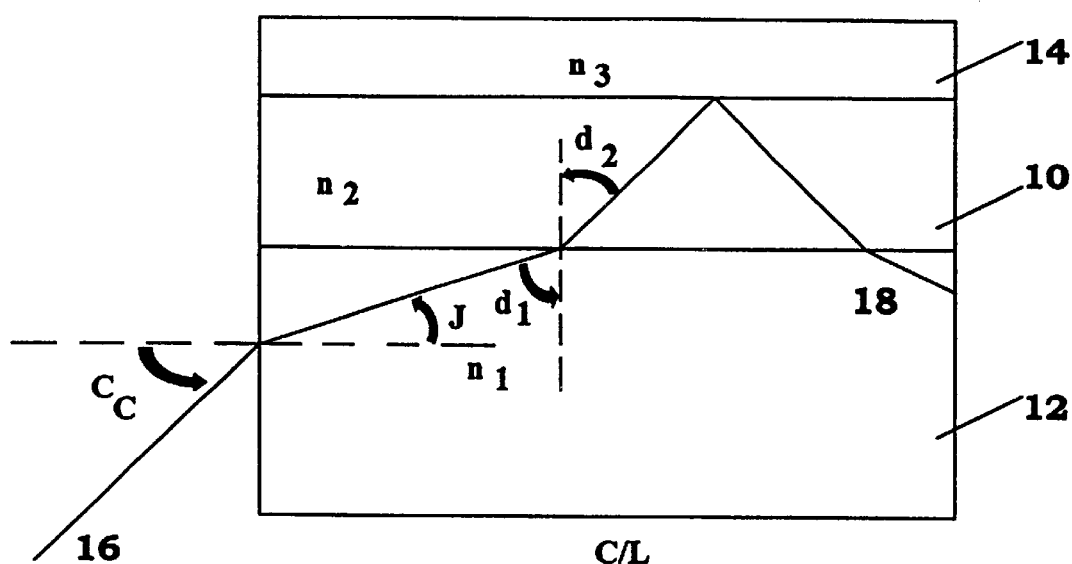
FIG. 3 is an illustration of an optical path in a dual cladding optical waveguide sensor along with external and interior (J, $d_1$, $d_2$) angle relationships. Here, the refractive indices are $n_2 \geq n_1 > n_3$ for inner layer, fiber optic core, and outer cladding layers, respectively.

The dual clad configuration of the present invention takes advantage of the simplicity of doping a cladding material while addressing the need for specific optical requirements in the outer cladding of fiber optics. In the present invention, as shown in FIGS. 1–3, a thin film of a material, e.g., polymer, comprising a sensing reagent 10 is deposited on a fiber, rod or slide waveguide 12 ("waveguide core") and subsequently overcoated with reflective cladding material 14. The intermediate sensing layer must be of good optical quality but need not have a refractive index less than that of fused silica or other core material, e.g., but not limited to, organic core materials; it does not act as cladding, but merely as a host matrix for an active reagent. In some embodiments, this host matrix is transparent to radiation transmitted by the waveguide core while in other embodiments, the host matrix is transparent to energy emitted by an active agent which is subsequently transmitted to the waveguide core. Indeed, in most embodiments, such as that outlined further below, a relatively high refractive index for this intermediate layer is advantageous to the sensitivity of the device. The lower refractive index outer cladding continues to perform its regular function of reflecting the propagating light down the fiber optic.

The transmitted wave 16 in the waveguide transits the inert carrier and samples any developed active agent response in a normal absorption mode 18. Active agent responses comprise, for example, changes in color and/or luminescence (e.g., fluorescence, phosphorescence, or chemiluminescence). The outer cladding provides a separate overlayer and the introduction of the intermediate, reagent-containing layer has little influence on the waveguide's performance (if it does not absorb or scatter the transiting light). The specific details of this particular "dual cladding" embodiment of the present invention's waveguide approach are described in detail below. Note that excitation of the fiber optic guide is in a normal mode of the core, not in an annular mode of the intermediate layer. Annular mode excitation is also possible using apparatuses and methods of the present invention, although, such embodiments require additional features to direct "waveguide" transmission into an annular region.

As applied to environmental sensors, a preferred embodiment of a dual cladding configuration comprises a reactant dye-doped intermediate layer comprising a refractive index greater than that of fused silica or other core material. A second reflecting cladding layer is then applied over the inner layer to form the clad waveguide. The outer layer refractive index establishes the acceptance angle for total internal reflection and the presence of the intermediate layer has no influence on this parameter. For this embodiment, as well as some others, apparatus sensitivity and sensitivity range depend in a complicated way on length and thickness of inner layer cladding, fiber optic diameter, and acceptance angle (or illumination angle). Sensitivity is also influenced by the nature by which the outer layer transmits, and/or transforms, an environmental stimulus, for example, permeability of the outer layer (for chemical sensors) and solubility of the analyte in the sensor layer are parameters that may affect sensitivity. The behavior of the optical variables is derived analytically in the following section.

Dual Coating Optics—Sensitivity Calculation (Absorption Case)

FIG. 3 is an illustration of the path of an entering light ray 16 in a dual-coated optical light guide. Refractive index requirements for this operational mode are that $n_2 \geq n_1 > n_3$, where $n_1$ is the index of refraction of the core 12 material and $n_2$ that of the inner sensor layer 10 with a cladding 14 index, $n_3$. The critical condition for operation ($n_2 \geq n_1 > n_3$) is assumed.

A calculation of the external critical angle for the mode and the variation of effective pathlength (sensitivity) with illumination angle follows. In this treatment, the exterior angles refer to the entrance of light into the optical fiber core remote from the dual clad segment.

The critical angle for configuration at the interface between the intermediate layer and the cladding is given by:

$$\sin d_2 = n_3/n_2 \tag{1}$$

for the interface between the interior guide and the interlayer:

$$n_1 \sin d_1 = n_2 \sin d_2 \tag{2}$$

giving, at the critical angle $$\sin d_1 = (n_2 n_3)/(n_1 n_2) = n_3/n_1 \tag{3}$$

In these equations, $d_1$ is the angle from the normal of the critically transmitted ray in the core, $d_2$ is the angle that ray makes in the inner layer, and $n_1$, $n_2$, and $n_3$ have their previous significance.

Note that Equation 3 is the same result one derives for the critical angle between the interior and the cladding in the absence of an intermediate layer. From this simple model it is apparent that the external critical angle ($c_c$) is also given for both cases by:

$$\sin c_c = (1/n_{air})(n_1^2 - n_3^2)^{0.5}. \tag{4}$$

In Equation 4, $n_{air}$ is the refractive index of air.

An expression for the effective pathlength in the coating (intermediate layer) as a function of coating thickness, fiber diameter, and entrance (exterior) angle follows. In these equations, T is the coating thickness, R is the fiber radius, and c is the illumination entrance angle.

From FIG. 3, the pathlength ($P_f$) per reflection in the film is $$P_f = 2T/\cos d_2 \tag{5}$$

the length between reflections ($P_L$) is $$P_L = 2R[((n_1/n_{air})^2/\sin^2 c) - 1]^{0.5}. \tag{6}$$

The pathlength in the coating per unit length of rod or fiber is then given by $L = P_f/P_L$ (after suitable substitution for $\cos d_2$)

$$L = (T/R) \times (1/(AB)) \tag{7}$$

where $$A = [1 - (n_1/n_2)^2 \times (1 - (n_{air}/n_2)^2 \sin^2 c)]^{0.5}$$

and $$B = [(n_1/n_{air})^2/\sin^2 c - 1]^{0.5}.$$

Equation 7 shows only one simplifying assumption; that the inner layer coating is thinner than the fiber diameter. Layers thicker than the fiber core diameter also perform satisfactorily but their sensitivity must be predicted from a modified calculation. From this calculation and using data developed for thin film material, the design parameters for "optrodes" for a specific sensitivity or range of response are defined. This dual cladding design is unique to present invention and is a significant innovation in sensor technology.

In addition to increased sensitivity associated with the thickness multiplication shown above, the elaborated preferred embodiment of the present invention allows separation of the properties necessary for function into three materials regions. These regions are: the core material, chosen to give very low optical attenuation; the inner cladding, chosen to give good permeation for analyte and/or good solubility for sensitizer; and the outer, reflective layer, chosen for low index of refraction, high toughness, and good transmission of a desired environmental stimulus, for example, analyte permeation for chemical sensor applications.

Dual Coating Optics-Sensitivity Calculation (Luminescence Case)

For the case of luminescence (e.g., fluorescence, phosphorescence, chemiluminescence) within the inner layer, two approximations are used to derive the sensitivity for light detection. The first case uses a planar guide to estimate the collection efficiency. For thin inner layers, the planar approximation allows a good estimation of the fraction captured; it is an upper limit.

In the planar model, the light that propagates in the core is calculated from the critical angle for a core/cladding interface, the same critical angle derived above for the absorption case (See Equation 3, above).

Light with emission angles greater than this value are either trapped in the inner layer and do not propagate in the core or are lost by transmission through the cladding. The fraction that will propagate in the core is given by:

$$F_P = 1 - (1 - (n_3/n_1)^2)^{0.5} \tag{8}$$

For typical refractive indices of core ($n_1 = 1.41$) and outer cladding ($n_3 = 1.38$), about 50% of the light emitted in the inner layer will propagate in the core. By careful shaping of the ends of the inner layer, it is possible to force the light propagating in the inner layer alone to be captured by the core and increase the light yield.

In cylindrical geometry, where the inner layer is comparable to or thicker than the core, a different approximation must be used. In this case, the fraction captured varies from the outer region of the inner layer where it has the above value ($\approx 50\%$) to the value at the inner layer/core interface. At the inner layer/core interface (for a small diameter core) the fraction propagating in the core is:

$$F_P = 1 - n_3/n_1 \tag{9}$$

Here a typical value for capture is 10–11%. The sensitivity is then related to the position within the coating thickness by:

$$F_P = 2\pi R L((F_{PO} - F_{PI})(R - R_I)/(R_O - R_I) + F_{PI}(R - R_I)/(R_{O-RI}))/V \tag{10}$$

where $F_{PO}$ is the fraction captured at the outer surface of the inner layer, $F_{PI}$ is the fraction captured from luminescence at the inner layer/core interface, $R_O$ is the radius of the inner layer/cladding interface, $R_I$ is the core radius, R is the radius where the luminescence takes place, and V is the volume of sensor (luminescer) in the length L of sensor.

To estimate the mean fraction of light captured, this expression must be integrated over all possible positions from which luminescence can occur. For typical values of refractive indices, the cylindrical geometry should allow about 35–40% of the emitted light to be captured and propagate in the fiber optic core.

This configuration does not allow light that propagates in the inner layer to propagate in the core as well. With suitable shaping of the sensor ends, some of this light is trapped in the core region. This assumes that the core is operating far from its propagation wavelength cutoff (multimode operation). Clearly, a luminescence fiber optic sensor of dual cladding structure harvests a substantial fraction of the available light from fluorescence, phosphorescence, or chemiluminescence.

Inner layers formulated with selected chemical sensing, scintillator and/or ionizing radiation dosimetry materials doped into hosts, e.g., polymer materials, are described below. Derivatized poly(dimethylsiloxane) is used as an inert reflective cladding (outer cladding) and fused silica is used for the supporting fiber.

EXAMPLE

The following apparatuses are described below for application as dosimeters for ionizing radiation.

An absorption mode dosimetry apparatus was fabricated by removal of the cladding from a low hydroxyl, high purity fused silica core fiber (commonly 0.5 to 0.05 millimeters in diameter) for a length of approximately 1 centimeter. The exposed core 12 was treated with an adhesion promoter commonly known in the art, for example, but not limited to, chromic acid, potassium hydroxide-methanol, triethoxymethylsilane coupling agent, plasma treatment with air and $CO_2$. After exposing the optical waveguide core 12, a radiation sensitive polymer layer 10 was deposited on the core and overcoated with a cladding layer 14 of sufficient thickness to act as both cladding and buffer.

As shown in FIG. 1, an ionizing radiation sensor was fabricated whose sensitivity was controlled by altering the dimensions of the coated region and by changing the fiber optic core diameter. Sufficient length of preformed fiber optic waveguide was retained on both ends of the sensor region to act as leads to the reading optics and electronics. Leads (many meters long) were used to allow the reader and its associated electronics to be remote from the radiation field to be measured. The sensor was then read by comparing the transmission of the assembly at the peak of the radiation developed absorption band and in a spectral region where no absorption was developed on irradiation. The optical density developed in the absorption band indicated the deposited dose from the radiation.

A second embodiment of the device is illustrated in FIG. 2. It was fabricated as follows: The buffer and cladding were removed from one end of low hydroxyl, high purity fused silica fiber optic waveguide to reveal a length of about 0.5 centimeter of the core. The exposed core 12 was then cleaned and surface activated as described above. Here the sensing layer 10 was formed by applying the coating of the first illustration or by applying a solution of a fluorescent dye in a suitable polymer host. The intermediate layer thus applied was trimmed to the desired length for the sensitivity or spatial resolution required and a cladding/buffer layer 14 overcoated. It was advantageous to polish and coat the reflectance end of the device with a metallic reflector 20 to achieve best performance. This is accomplished by coating with metallic silver (e.g., by any of the solution coating processes known in the art of mirror fabrication or by vacuum metallization using a variety of metals).

This apparatus was used as in the first example, by measuring the light absorbed by the dosimetry formulation, or by measuring the emission intensity of the dye-doped polymer. In the first of these two alternatives, a response characteristic of the total dose was given which could be preserved for re-reading many times. For the second, the fluorescence sensor, the response was transient and represents the dose rate with response times that can be less than $10^{-9}$ seconds. In either case, both dose rate and total dose were indicated by the reading electronics through electronic manipulation of the signals received.

Sensors of the present invention are also useful as chemical sensors for sensing, for example, hydrocarbons in media such as, but not limited to, air, ground water and/or soils. A chemical sensor of the present invention was made for sensing aromatics comprising a fused silica fiber core waveguide. An outer cladding comprising polydimethylsiloxane was used that allowed for transport of hydrocarbons. An intermediate layer was formed comprising poly (cyclohexyl methacrylate) doped with tetracyanoethylene. The dopant acted as an acceptor while the hydrocarbon acted as a donor wherein an acceptor-donor charge transfer complex absorbed radiation differently than acceptor and donor alone. This allowed for monitoring of complex formation and concentration. For instance, a tetracyanoethylene (acceptor) and benzene (donor) complex was monitored at a wavelength of 362 nm. The sensor also allowed for qualitative determinations because of differences in radiation absorption properties of acceptor/donor complexes for different aromatic hydrocarbon donors.

Sensors of this example are extremely versatile and useful in a variety of configurations, such as in the aforementioned transmission and reflective configurations. Furthermore, in addition to a tetracyanoethylene dopant, other dopants are useful, alone or in combination, to create chemical sensors having differing response characteristics. Other useful dopants include, but are not limited, to 2,4,7-trinitrofluorenone and 7,7,8,8-tetracyanoquinodimethane. In general, the dopants, produce a response to an environmental stimulus, such as, the presence of a hydrocarbon. In this preferred embodiment of the present invention, a response is detectable through monitoring of electromagnetic radiation, particularly, radiation transmittable through use of fiber optic waveguides, e.g., ultraviolet radiation.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An optical waveguide sensor comprising:
    a waveguide core;
    a reflective cladding; and
    at least one intermediate layer positioned between said waveguide core and said reflective cladding wherein said at least one intermediate layer comprises a material responsive to at least one environmental stimulus selected from the group consisting of ultraviolet radiation and ionizing radiation; and
    wherein refractive indices of said core ($n_1$), said at least one intermediate layer ($n_2$) and said reflective cladding ($n_3$) obey the relationship $n_2 \geq n_1 > n_3$.

2. The waveguide sensor of claim 1 wherein said material responsive to at least one environmental stimulus comprises a dye that changes optical absorption characteristics upon exposure to ionizing radiation.

3. The waveguide sensor of claim 2 wherein said sensor comprises a radiation dosimeter.

4. The waveguide sensor of claim 1 wherein said sensor comprises a segment of a waveguide wherein said waveguide comprises the waveguide core and a reflective cladding.

5. The waveguide sensor of claim 1 wherein said sensor comprises a terminal end of a waveguide wherein said waveguide comprises a waveguide core comprising a terminal end and a reflective cladding.

6. The waveguide sensor of claim 5 additionally comprising a reflective cap and at least one intermediate layer positioned between said terminal end of said waveguide core and said reflective cap.

7. An optical waveguide sensor comprising:
    a waveguide core comprising an outer surface; and
    a layer positioned on said outer surface of said waveguide core wherein said layer comprises a material responsive to at least one environmental stimulus selected from the group consisting of ultraviolet radiation and ionizing radiation.

8. The optical waveguide of claim 7 wherein said layer comprises an outer surface and said outer surface contacts a medium comprising a refractive index greater than the refractive index of said waveguide core.

9. The waveguide sensor of claim 7 wherein said material responsive to at least one environmental stimulus comprises a dye that changes optical absorption characteristics upon exposure to ionizing radiation.

10. The waveguide sensor of claim 9 wherein said sensor comprises a radiation dosimeter.

11. The waveguide sensor of claim 7 wherein said sensor comprises a segment of a waveguide.

12. The waveguide sensor of claim 7 wherein said sensor comprises a terminal end of a waveguide.

13. The waveguide sensor of claim 12 comprising at least one intermediate layer positioned adjacent to said terminal end.

14. A method for fabricating an optical waveguide sensor comprising the steps of:
    a) providing a waveguide core having an outer surface; and
    b) affixing an intermediate layer to the outer surface of the waveguide core wherein the intermediate layer comprises a material responsive to at least one environmental stimulus selected from the group consisting of ultraviolet radiation and ionizing radiation.

15. The method of claim 14 further comprising the step of affixing a reflective cladding to the outer surface of the intermediate layer.

16. The method of claim 14 wherein the affixing step comprises providing a material responsive to at least one environmental stimulus comprising a dye that changes optical absorption characteristics upon exposure to ionizing radiation.

17. The method of claim 16 wherein the sensor is a radiation dosimeter.

18. The method of claim 14 wherein the providing step comprises providing a segment of a waveguide wherein the waveguide comprises the waveguide core and a reflective cladding.

19. The method of claim 14 wherein the providing step comprises providing a terminal end of a waveguide wherein the waveguide comprises a waveguide core comprising a terminal end and a reflective cladding.

20. The method of claim 19 wherein the providing step further comprises providing a reflective cap and at least one intermediate layer positioned between the terminal end of the waveguide core and the reflective cap.

* * * * *